United States Patent [19]

(12) United States Patent
Mehier

(10) Patent No.: US 7,753,871 B2
(45) Date of Patent: Jul. 13, 2010

(54) APPARATUS FOR INJECTING STEAM INTO A HUMAN OR ANIMAL

(75) Inventor: Henri Mehier, Lyons (FR)

(73) Assignee: Centre d'Affaires International (FR)

( * ) Notice: Subject to any disclaimer, the term of this patent is extended or adjusted under 35 U.S.C. 154(b) by 166 days.

(21) Appl. No.: 12/119,361

(22) Filed: May 12, 2008

(65) Prior Publication Data

US 2008/0281267 A1    Nov. 13, 2008

Related U.S. Application Data

(60) Provisional application No. 60/939,920, filed on May 24, 2007.

(30) Foreign Application Priority Data

May 10, 2007    (FR)    .................................. 07 54985

(51) Int. Cl.
*A61M 37/00* (2006.01)
*A61M 1/00* (2006.01)
(52) U.S. Cl. .......................... 604/26; 604/114; 604/151
(58) Field of Classification Search .................... 604/23, 604/26, 507, 508, 113, 114; 606/46
See application file for complete search history.

(56) References Cited

U.S. PATENT DOCUMENTS 6,537,248 B2 *    3/2003    Mulier et al. ................ 604/114
2003/0109869 A1 *    6/2003    Shadduck .................... 606/41

* cited by examiner

*Primary Examiner*—Nicholas D Lucchesi
*Assistant Examiner*—Leah Stohr
(74) *Attorney, Agent, or Firm*—Cantor Colburn LLP

(57) ABSTRACT

Apparatus intended for the injection of pulsed steam into a human or animal vessel comprising
    an injection unit sending pulses of cold water into a handpiece,
    a handpiece temporarily attached to an injection unit within which there is a metal tube, of external diameter between 200 µm and 1,000 µm and internal diameter between 100 µm and 500 µm, the metal tube having its distal end coiled to form a spiral, the tube being sheathed with a material of resistivity such that only the spiral heats to a temperature transforming water from the liquid phase into the vapor phase,
    a means of distributing the steam into the vessel intended to be connected in a reversible manner to the distal end of the handpiece.

10 Claims, 3 Drawing Sheets

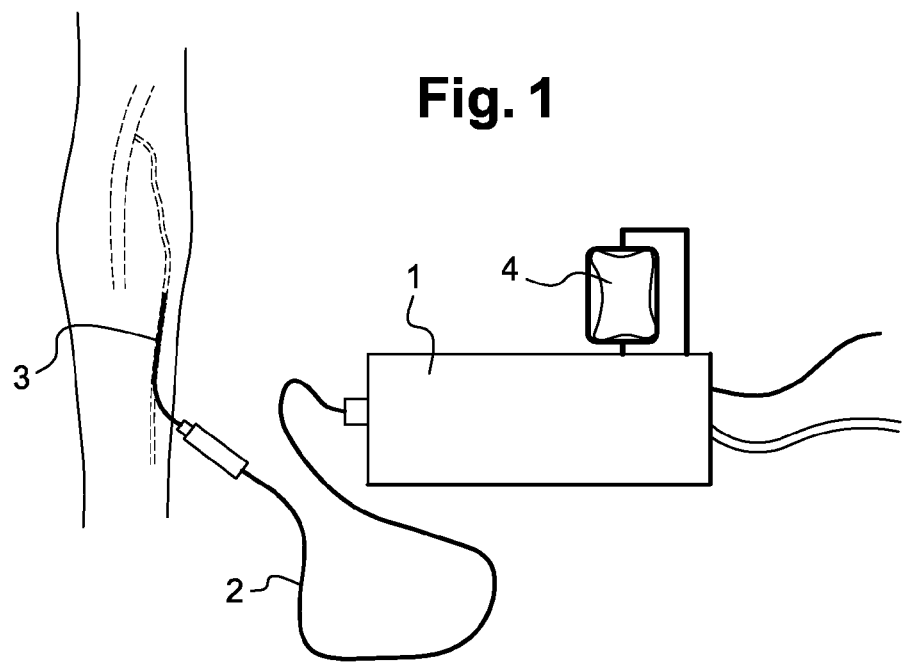
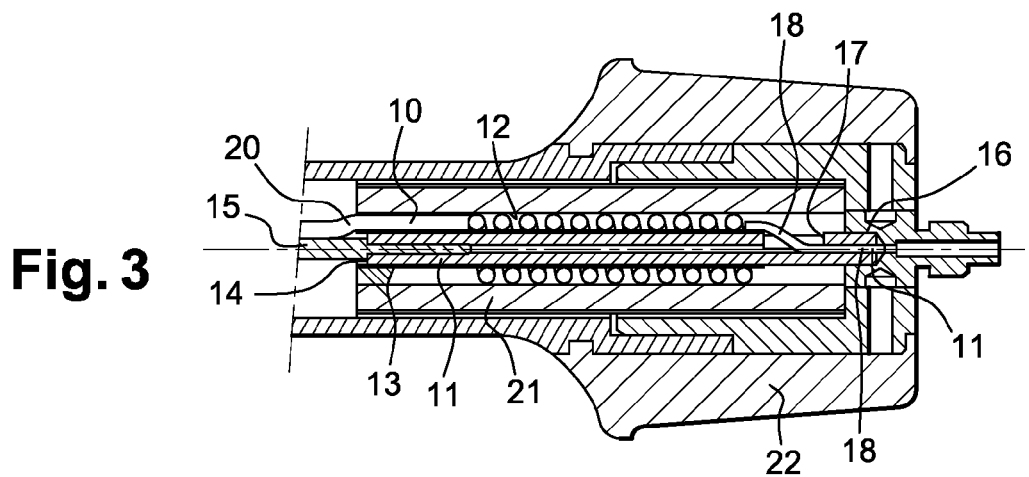
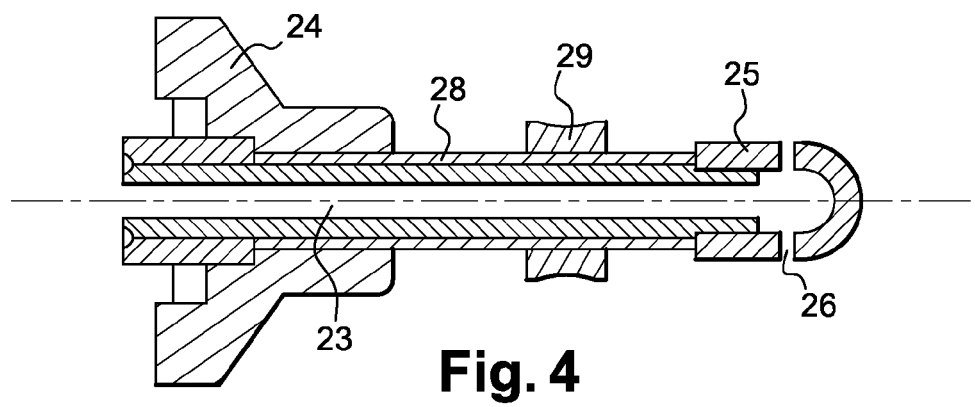

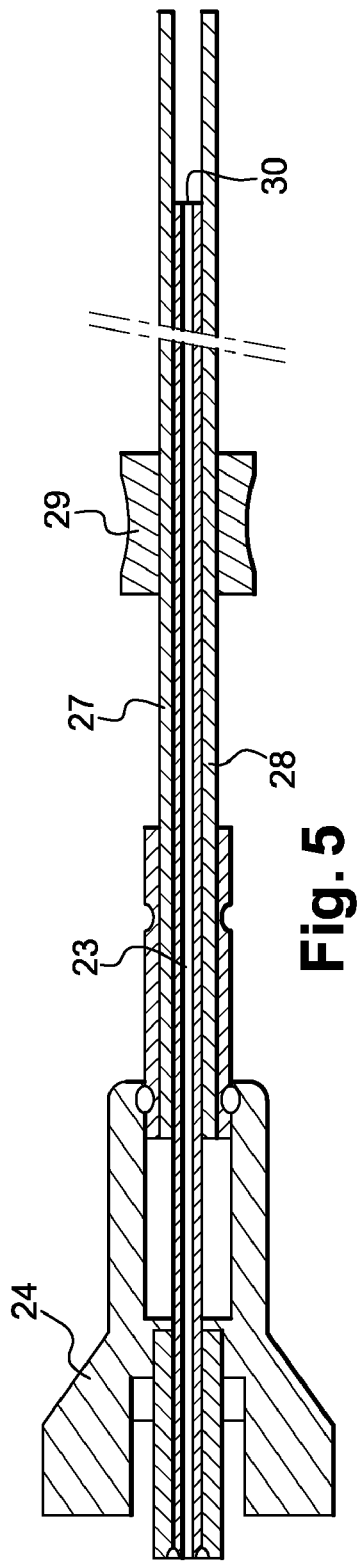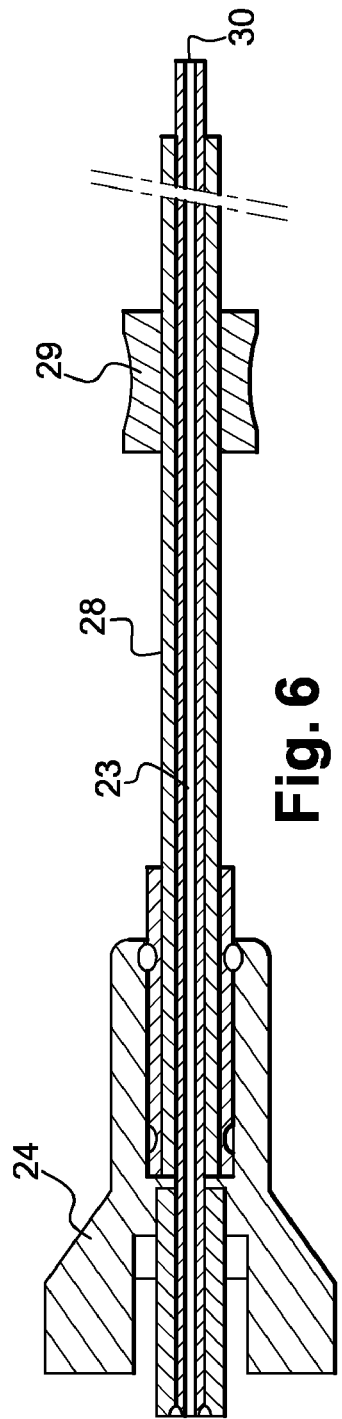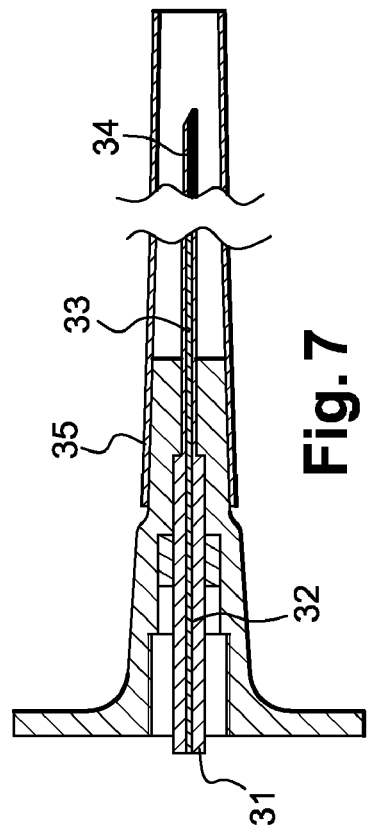

APPARATUS FOR INJECTING STEAM INTO A HUMAN OR ANIMAL

CROSS REFERENCE TO RELATED APPLICATION

This application claims the benefit of U.S. Provisional Patent Application Ser. No. 60/939,920 filed on 24 May 2007, the contents of which are incorporated by reference herein in their entirety.

TECHNICAL FIELD OF INVENTION

The invention concerns a new device for treating pathological venous or arterio-venous diseases, in particular varicose veins, hemorrhoids, arterio-venous shunts or other vascular malformations, by injecting steam via the endoluminal route. More precisely the invention concerns a device for injecting pulsed steam into a human or animal vein.

BRIEF DISCUSSION OF RELATED ART

The document US 2003/0109869 A1 describes a method for treating varicose veins. The proposed system consists of injecting steam directly into the vein, so as to destroy a varicose vein by heating the collagen present in its walls. In practice, the transformation of the water into steam occurs directly in the vein, the water being heated at the distal end of a catheter by an electric arc formed by an electrode rolled into a spiral.

This apparatus has several disadvantages.

The first is the high power requirement of the electric arc to transform the water into steam. Secondly, and above all, the catheters are consumable products and therefore not reusable from one patient to another. Bearing in mind the technical complexity of this type of catheter, this considerably increases the cost of the equipment and therefore of the procedure. To reduce this cost, it would seem best to transform the water into steam no longer in the consumable catheter but rather before this, i.e. at the point where the liquid is supplied to the catheter introduced into the vein.

In another field concerning ablation or cauterization of tissue, the document WO 02/069821 describes an apparatus in which the transformation of water into steam is performed in a handpiece outside the organism. In the proposed system, the handpiece contains a tube with two electrodes connected to a radio-frequency generator; the liquid passes the current between the two electrodes. The disadvantage of this system is having a tube without differential heating, which means that the tube is heated throughout its length. That being the case, not only is there a loss of heat, but in addition and above all, given the heating temperatures, holding the handpiece can be uncomfortable for the user thus hindering the procedure. This phenomenon is aggravated by the continual production and transfer of steam which results in overheating, not only for the user but more particularly, for the patient.

Finally, the Applicant's own document WO 2006/108974 describes an apparatus allowing pulsed injection of steam not into a vein, but directly into tissues, particularly for treating tumors. In the proposed device, heating does not occur in the handpiece, i.e. outside the organism, but directly in the catheter in contact with the tissue. Unlike in the previous document, here the heating is differential, i.e. the transformation of the water into steam occurs exclusively at the distal end of the tube inserted into the organism. While this apparatus may provide effective treatment for tumors, it does have the major disadvantage of being relatively expensive, in as far as miniaturization of the heating system in the tubes in contact with the organism (i.e. the consumable items) is very costly.

In other words, the problem, that the invention intends to solve, is to develop an apparatus for treating in particular varicose veins and hemorrhoids by injecting steam via the endoluminal route, in which the heating system and thus the system for transforming the water into steam is moved outside the organism.

BRIEF SUMMARY OF THE INVENTION

The produces a device in which the change in state of the liquid occurs in the handpiece, while complying with the two requirements of comfort for the surgeon when holding the handpiece and effective heating of the vessel, particularly a vein where it is varicose or the hemorrhoid to be treated, without burning the patients skin.

The Applicant has succeeded in developing a handpiece for this purpose in which the transformation of water into steam occurs exclusively at the distal end of the handpiece in an area which is not in contact with the surgeon's hand. All the parts of the apparatus are designed and arranged to allow the steam to be administered in pulses to the distal end of the device, i.e. to the vessels to be treated, the pulsing permitting the calories to be transferred rapidly from the handpiece to the end of the means of distribution thus providing calories locally as rapidly as possible in order to reduce undesirable thermal losses.

The invention relates, therefore, to an apparatus producing pulsed injections of steam into a human or animal vessel comprising:

an injection unit sending pulses of cold water into a handpiece, a handpiece temporarily attached to the injection unit within which is a metal tube in which the cold water is transformed into steam, a means of distributing the steam into the vessel intended to be connected in a reversible manner to the distal end of the handpiece, characterized in that the metal tube:

has an external diameter of between 200 µm and 1,000 µm, advantageously in the order of 800 µm, and an internal diameter between 100 µm and 500 µm, advantageously in the order of 250 µm, has a distal end coiled into a spiral, and in that the two ends of the tube are connected to an electric supply, the portion of the tube between its proximal end and the proximal end of the spiral being sheathed with a material, advantageously copper braid, with resistivity such that only the spiral heats to a temperature allowing the water to change from the liquid to the vapor phase.

In other words, the Applicant has succeeded in producing a system in which differential heating is possible in the handpiece, i.e. in a semi-consumable part, thus decreasing the cost of the apparatus. In practice, the semi-consumable part is reusable for about twenty procedures. In addition, the particular configuration of the microtube in which the water circulates in the handpiece allows the vapor state to be maintained from the distal end of the handpiece to the distal end of the means of distribution.

In practice and according to another characteristic, the spiral is formed around a part of a metal tube of low electrical resistance, in practice lower than 0.5 ohm, allowing electrical current to pass without heating. The tube's proximal end in contact with the spiral is sheathed in an electrical and thermal insulating material, the conducting part of the tube being connected to the electrical supply providing the current, while its distal end has no electrical and thermal insulating sheath and is in contact with the distal end of the tube through which the liquid runs.

Moreover, taking into account the diameter of the tube through which the liquid flows and the size of the handpiece, which must be easy for the surgeon to use, the length of the tube coiled to form a spiral is between 10 and 30 cm, advantageously in the order of 20 cm.

To avoid risks of short-circuiting and to decrease as much as possible the temperature to which the distal end of the handpiece is heated, the distal end of the tube in the area where the spiral is located is sheathed with an electrical and thermal insulating layer.

Advantageously, to further improve the thermal insulation, the distal end of the handpiece, in the area where the spiral is located, is composed of a thermal insulating material and in particular, silicone.

To allow the surgeon a certain freedom of movement, the handpiece is advantageously irreversibly connected to an extension linking it to the cold water injection unit. In this configuration, the apparatus consists of a non-consumable device (injection unit), semi-consumable items (handpiece and extension) and consumable items (means of distribution).

There are three distinct forms of the means of distribution.

In the first two instances, the means of distribution is in the form of a metal tube of internal and external diameters advantageously less than those of the tube located in the handpiece, between 100 and 200 µm, advantageously 150 µm, for the internal diameter and between 250 and 500 µm, advantageously 350 µm, for the external diameter, thus giving it a certain flexibility and reducing thermal exchange.

In a first embodiment, the distal end of the microtube is closed, advantageously with a rounded stainless steel element added to the said end, the tube having near its own distal end or on the additional element at least one transverse opening. To avoid necrosis of the vessel walls, the whole surface of the tube is covered with a layer of a thermal insulating material such as and in particular PTFE, PEEK, polyimide or silicone, advantageously PTFE, except for any transverse opening.

In another embodiment, the microtube is sheathed with a thermal insulating material; this sheath is not fixed but can be displaced along the microtube. In this case, the insulating sheath is longer than the microtube, which, because of the flexibility of the sheath, avoids perforating the vessel with the microtube when the latter is introduced into the said vessel. In practice, the microtube has an opening at its terminal end to deliver the pulses of steam.

In these two embodiments, the microtube is marked along its whole length, in practice every centimeter, indicating to the operator the length of microtube remaining in the vessel as it is withdrawn from the latter.

In another embodiment, the means of distribution is not in the form of a microtube but of a needle, which is covered, at least over the area in contact with the vessel, with a thermal insulating material, such as PTFE. In practice, the needle is composed of three sections decreasing in size obtained by grinding the external cross-section from the proximal end to the distal end, and respectively: a proximal portion with external diameter between 1.4 and 1.9 mm, a middle portion with external diameter between 1 and 1.3 mm, a distal portion with external diameter between 0.5 and 0.8 mm, The internal diameter of the needle is constant and between 0.1 and 0.25 mm, advantageously equal to 0.15 mm.

Obviously, the means of distribution and the handpiece are connected by any suitable means known to those skilled in the art.

The injection unit is like the unit described in document WO 2006/108974 included here for reference. More particularly, the injection unit is in the form of a chamber containing the water to be injected, in which there is a hydraulic piston driven by an electric, pneumatic, piezoelectric or mechanical piston, the activation and/or force and/or speed of movement of which are determined by the hydraulic piston according to the rhythm, volume and pressure required for injection of the substance into the handpiece. The injection unit can also be combined with a cold water storage unit.

The invention also concerns a method of treating venous or arterio-venous diseases, in particular varicose veins, hemorrhoids and arterio-venous shunts, and more generally vascular malformations, by injecting pulses of steam into the vessels (veins and/or arteries) via the endoluminal route using the apparatus previously described. The advantage of the apparatus is that it distributes steam homogeneously in vessels over several centimeters (in practice 4 to 5 cm), which avoids any risk of carbonization or perforation of the wall such as could occur with the apparatus described earlier in document US 2003/0109869 or in other existing thermal techniques, generating localized heat.

BRIEF DESCRIPTION OF THE SEVERAL FIGURES

The invention and the advantages resulting from it are better illustrated by the following examples of embodiments and the attached figures.

FIG. 1 is a diagram of the apparatus of the invention.

FIG. 3 is a detailed representation of the distal end of the handpiece, shown in FIG. 2.

FIG. 4 illustrates the means of distribution in a first embodiment.

FIGS. 5 and 6 are diagrams of the means of distribution in a second embodiment.

FIG. 7 is a diagram of the means of distribution in a third embodiment.

DETAILED DESCRIPTION OF THE INVENTION

Figure 2:
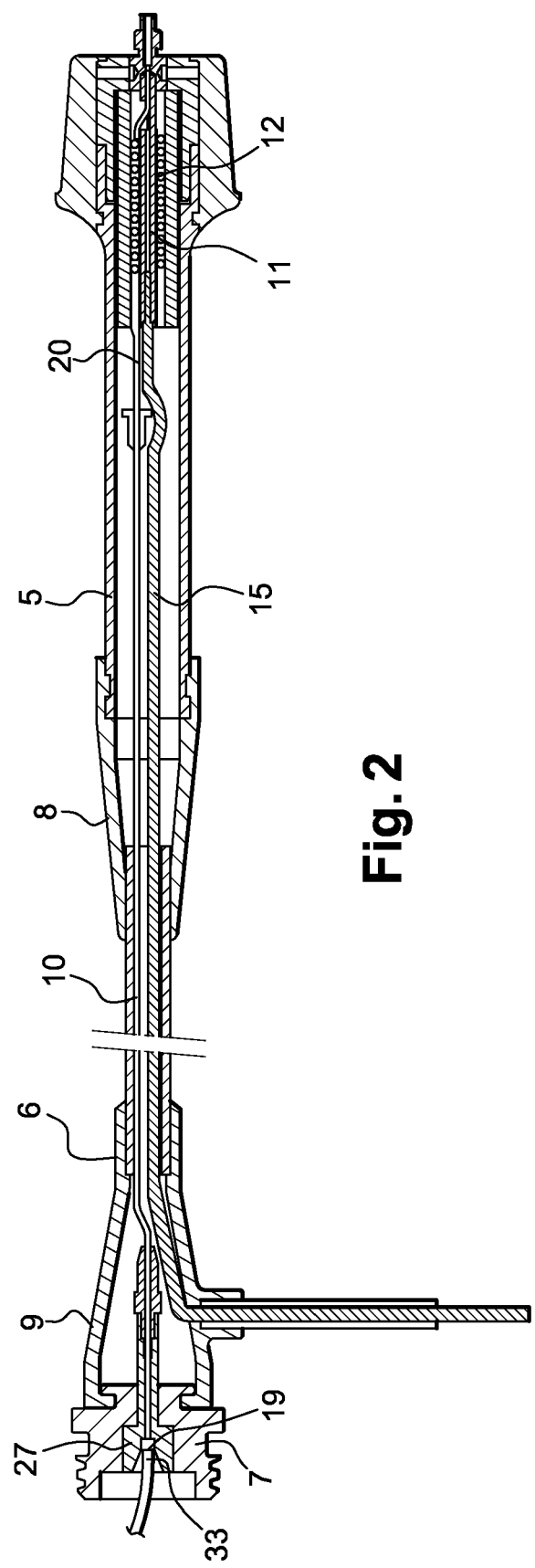
FIG. 2 is a cross-section of the handpiece and the extension of the invention.

FIG. 1 is a diagram of the apparatus of the invention. As this figure shows, the apparatus consists of three basic elements: a pulsed cold water injection unit (1), an extension-handpiece combination (2) at the distal end of which the water is transformed into steam, a means for distributing the steam into the vein in the form of a catheter or microtube (3).

In practice, the injection unit is in addition associated with a water storage bag (4).

The cold water pulse generator does not need to be described in detail and is like the one illustrated in the previously cited submission WO 2006/108974 A1. In practice, the injection unit is in the form of a chamber containing a substance to be injected, in this case cold water, in which there is a small diameter hydraulic piston, of the order of 3 to 5 mm, driven by a larger diameter electric, pneumatic, piezoelectric or mechanical piston, of the order of 50 to 80 mm, the activation and/or running and/or force and/or speed of movement of which are determined by the hydraulic piston according to the rhythm, volume and pressure required for injection of the substance into the extension-handpiece combination.

To avoid water returning into the injection unit after injection of this water into the handpiece-extension combination, the injection unit contains two anti-return valves (not shown). As already stated, the pressure at which the substance is injected depends on the speed of displacement and the force of the pistons, e.g. pneumatic pistons, which are also programmed.

The means of distributing the steam into the vessel is separated from the injection unit by a handpiece-extension combination (2) shown in FIG. 2. More precisely, the combination shown consists of a handpiece (5), an extension (6) and a means of connection (7) to the injection unit in the form of a screw thread. The handpiece (5) and the extension (6) are generally tubular in shape. The connection between the extension and the handpiece on the one hand and the screw thread (7) on the other is made using the intermediate parts (8, 9). Parts 8 and 9 are fitted so as to make disassembly impossible. The extension-handpiece combination thus forms a semi-consumable item. In practice, the extension can be 1.5 to 5 m long whilst the size of the handpiece is about 10 to 20 cm.

According to the invention, a tube (10) runs through the extension-handpiece combination in which the liquid circulates. The tube is made of stainless steel and has an internal diameter of 250 µm and an external diameter of 800 µm. The material forming the tube has a resistivity of 72 µΩ/cm.

As is shown in FIG. 3, the distal end of the tube (10) is coiled around a portion of stainless steel tube (11) of low resistance forming a spiral (12), in practice 20 cm long. The portion of stainless steel tube (11) in contact with the spiral (12) is covered by an electrical and thermal insulating sheath (13). The proximal end (14) of the portion of tube (11) is in contact with an electrical conductor (15) connected to the positive terminal of an electrical source (not shown). The distal end (16) of the portion of tube (11) has an opening (17) allowing the distal end (18) of the spiral (12) to pass so as to be in contact with the electrical conductor formed by the portion of low resistance, in practice less than 0.5Ω, stainless steel tube (11). As FIG. 3 shows, the distal end of the portion of tube (11) has no insulating sheath thus allowing current to pass from the stainless steel tube (11) into the spiral (12). To allow heating to occur only in the spiral part of the tube (10) and not in the straight part between its proximal end (19) at the injection unit outlet and the proximal end (20) of the spiral (12), the straight part has a low resistivity braided copper sheath. The screw thread (7) provides the hydraulic connection which at the same time serves as electrical ground (27). In other words, the current circulates in the electrical conductor (15), then in the spiral (12) to return via the tube (10) to ground (27).

According to another characteristic, the spiral (12) has an electrical and thermal insulating sheath (21). Moreover, the distal end of the handpiece is fitted with a silicone part (22) which avoids the handpiece heating up too much.

FIG. 4 is a diagram of the means of distribution in a first embodiment. In this configuration, the means of distribution is in the form of a microtube (23) of internal diameter equal to 150 µm and external diameter equal to 350 µm. This microtube (23) is connected to the distal end of the handpiece by any appropriate means shown in the diagram by number 24. According to a basic characteristic, the distal end of the microtube is closed by an additional stainless steel part (25) with a transverse opening (26) allowing the passage of steam. In practice, with the exception of the additional part, the microtube is covered with a thermal insulating substance in PTFE and/or PEEK (28). In addition, near its proximal end the microtube has a means for gripping it (29) to aid the surgeon as he inserts the microtube into the vessel.

In the embodiments shown in FIGS. 5 and 6, the PTFE sheath (28), arranged around the microtube (23) is no longer fixed, but mobile. In this hypothesis, the microtube is not closed and therefore has a terminal opening (30).

FIG. 5 shows the means of distribution at the time it is inserted, while FIG. 6 shows the same means of distribution at the time of treatment.

As these figures show, the sheath or PTFE tube (28) is longer than the microtube to avoid any perforation in the area to be treated by the microtube when it is inserted. In the treatment position, the PTFE tube is withdrawn backwards using the part (29) which remains outside of the organism. It should be understood that the connection between the proximal end of the microtube and the distal end of the handpiece is made by any known means, represented diagrammatically by number 24.

FIG. 7 is a representation of the means of distribution in a third embodiment. In this case, the microtube is replaced by a needle (31) of continuous internal diameter of 0.15 mm and with three distinct sections obtained by grinding, respectively: a proximal portion (32) of 1.6 mm external diameter, a middle portion (33) of 1.2 mm external diameter and a distal end (34) of 0.7 mm external diameter.

The part of the needle intended to be introduced into the vessel is covered by a Teflon sheath or silicone deposit (not shown). Moreover, during storage, the needle is surrounded by a protective tube (35) considerably longer than the needle.

As already stated, the apparatus of the invention is intended for treating venous or arterio-venous diseases and more particularly for the treatment of varicose veins or hemorrhoids. In practice, the generator is set to deliver pulses of water of a volume of between 50 and 100 µl, advantageously 70 µl, transporting between 30 and 100 J, advantageously in the order of 50 J.

The method of treatment will now be described in detail for varicose veins using a means of distribution in the form of a microtube (FIGS. 4 to 6).

A preliminary diagnostic evaluation of the pathology is made using Doppler ultrasound. The course of the vein to be treated and the point of introduction of the microtube delivering the steam are marked on the skin.

The number of pulses to be given per centimeter length of the vessel to be treated is determined depending on the diameter of the vessel. As an example, for a 12 mm diameter vein, two pulses of 70 µl of water are given, each pulse carrying 50 J of energy.

The treatment can then begin either under local or general anesthesia depending on the wishes of the patient.

The method of treatment consists first of all of puncturing the vessel, and more particularly the vein to be treated, using a needle positioned in a small catheter about 5 cm long, the surface of which has been Teflon treated, the needle being withdrawn after inserting the catheter at the surface of the skin. The microtube, in one of the configurations from FIG. 4, 5 or 6 above, is introduced into the catheter until the distal end of the microtube reaches the end of the vein to be treated.

The generator then sends pulses of cold water into the handpiece, which transforms these pulses into steam at a temperature of about 200° C. and the steam then passes through the microtube to its distal end.

Using the markings on the surface of the microtube, the operator progressively withdraws the microtube giving 1 or more pulses per centimeter depending on the diameter of the vessel. According to a basic characteristic, it is not necessary for the withdrawal to be continuous and regular, which means that the apparatus does not require an additional device automating withdrawal.

The apparatus can also be applied to the treatment of hemorrhoids.

In this case, the lesions are viewed using an anuscope. Forceps are then placed at the base of the hemorrhoid to interrupt the blood flow and limit heat transfer to the anal wall. A fine needle of the type previously described (FIG. 7) is introduced, surrounded by an insulating material to protect the mucosa from burns, all controlled visually. Heating is started and 1 to 3 pulses of steam are emitted. The needle is then withdrawn, the forceps opened and also removed. During the treatment, air or liquid cooling can be provided to protect neighboring structures. The anal mucosa can also be protected with a gel which may be anesthetizing.

The invention and the advantages resulting from it are clearly shown by the previous description. Particularly to be noted is the perfection of an apparatus suitable for injecting pulses of steam directly into a vein where the heating occurs in semi-consumable items rather than in consumable items.

In addition, one of the useful points of the technique perfected by the Applicant is being able to apply a uniform temperature over a length of 5 to 6 cm of vein, which allows the means of distribution to be withdrawn in successive steps. In contrast, other technologies, such as RF or laser treatment, produce localized heat with the risk of inducing localized necrosis along the wall of the vein.

Another advantage of the technique is its ability to treat both veins containing blood or emptied of blood, while laser treatment is used on veins containing blood and RF treatment is used on veins emptied of blood.

The invention claimed is:

1. Apparatus for injecting pulsed steam into a human or animal comprising:
   an injection unit (1) sending pulses of cold water into a handpiece (5),
   a handpiece (5) temporarily attached to the injection unit (1) within which is a metal tube (10) in which the cold water is transformed into steam,
   a means of distributing the steam intended to be connected in a reversible manner to the distal end of the handpiece, characterized in that the metal tube (10):
   has an external diameter between 200 µm and 1,000 µm and an internal diameter between 100 µm and 500 µm,
   has a distal end coiled to form a spiral (12),
   and in that two extremities of the tube are connected to an electric supply (27, 15), the portion of the tube between its proximal end (19) and the proximal end (20) of the spiral (12) being sheathed with a material of resistivity such that only the spiral heats to a temperature allowing the water to change from the liquid to the vapor phase.

2. Apparatus according to claim 1, characterized in that the spiral (12) is formed around a portion of a metal tube (11) of low electrical resistance of which: the proximal end (14) in contact with the spiral (12) is sheathed with an electrical and thermal insulating material (13), a conducting part of the tube being connected to the electrical supply providing the current, the distal end (16) has no electrical and thermal insulating sheath and is in contact with the distal end of the tube (10) through which the liquid runs.

3. Apparatus according to claim 1, characterized in that the length of tube rolled up to form a spiral (12) is between 10 and 30 cm, advantageously close to 20 cm.

4. Apparatus according to claim 1, characterized in that the distal end of the tube (10) in the area where the spiral (12) is located is sheathed in an electrical and thermal insulating layer (21).

5. Apparatus according to claim 1, characterized in that the distal end of the handpiece where the spiral is located is composed of a thermal insulating material, in particular silicone (22).

6. Apparatus according to claim 1 characterized in that the handpiece (5) is rigid and connected to a flexible extension (6).

7. Apparatus according to claim 1, characterized in that the means of distribution is in the form of a metal tube (23) of internal diameter between 100 and 200 µm and external diameter between 250 and 500 µm, the distal end of which is closed by an additional steel part (25) having at least one transverse opening (26), the whole surface of the tube being in addition covered with a layer of thermal insulating material (28).

8. Apparatus according to claim 1, characterized in that the means of distribution is in the form of a metal tube (23) of internal diameter between 100 and 200 µm and external diameter between 250 and 500 µm, the distal end of which is open (30), the tube being covered by a thermal insulating sheath (28) which can move along the tube and which is longer than the metal tube.

9. Apparatus according to claim 1, characterized in that the means of distribution is in the form of a needle (31) covered with a thermal insulating material at least over the area intended to be in contact, this needle having three sections decreasing in size obtained by grinding the external cross-section from the proximal end to the distal end, and respectively:
   a proximal portion with external diameter between 1.4 and 1.9 mm,
   a middle portion with external diameter between 1 and 1.3 mm,
   a distal portion with external diameter between 0.5 and 0.8 mm, the internal diameter of the needle being constant and between 0.1 and 0.25 mm, to advantage equal to 0.15 mm.

10. Apparatus according to claim 1 characterized in that the injection unit is in the form of a chamber containing the water to be injected, in which there is a hydraulic piston driven by an electric, pneumatic, piezoelectric or mechanical piston, the activation and/or force and/or speed of movement of which are determined by the hydraulic piston according to the rhythm, volume and pressure required for injection of the substance into the handpiece.

* * * * *